(12) United States Patent
Dubrul et al.

(10) Patent No.: US 6,699,260 B2
(45) Date of Patent: *Mar. 2, 2004

(54) TISSUE REMOVAL DEVICE AND METHOD

(75) Inventors: William Dubrul, Redwood City, CA (US); Richard Eustis Fulton, III, Grand Junction, CO (US)

(73) Assignee: Genesis Technologies LLC, Redwood City, CA (US)

( * ) Notice: Subject to any disclaimer, the term of this patent is extended or adjusted under 35 U.S.C. 154(b) by 198 days.

This patent is subject to a terminal disclaimer.

(21) Appl. No.: 09/819,350

(22) Filed: Mar. 28, 2001

(65) Prior Publication Data

US 2001/0011182 A1 Aug. 2, 2001

Related U.S. Application Data

(63) Continuation of application No. 09/189,574, filed on Nov. 11, 1998, now Pat. No. 6,238,412.
(60) Provisional application No. 60/065,118, filed on Nov. 12, 1997.

(51) Int. Cl.[7] .............................................. A61M 29/00
(52) U.S. Cl. ....................................... 606/200; 604/907
(58) Field of Search ........................... 606/200; 604/907

(56) References Cited

U.S. PATENT DOCUMENTS

| | | |
|---|---|---|
| 3,996,938 A | 12/1976 | Clark, III |
| 4,401,124 A | 8/1983 | Guess et al. |
| 4,582,061 A | 4/1986 | Fry |
| 4,869,259 A | 9/1989 | Elkins |
| 4,977,897 A | 12/1990 | Hurwitz |
| 5,048,530 A | 9/1991 | Hurwitz |
| 5,081,997 A | 1/1992 | Bosley, Jr. et al. |
| 5,213,569 A | 5/1993 | Davis |
| 5,221,269 A | 6/1993 | Miller et al. |
| 5,329,942 A | 7/1994 | Gunther et al. |
| 5,380,273 A | 1/1995 | Dubrul et al. |
| 5,383,466 A | 1/1995 | Partika |
| 5,490,521 A | 2/1996 | Davis et al. |
| 5,498,236 A | 3/1996 | Dubrul et al. |
| 5,518,498 A | 5/1996 | Lindenberg et al. |
| 5,549,626 A | 8/1996 | Miller et al. |
| 5,611,345 A | 3/1997 | Hibbeln |
| 5,713,848 A | 2/1998 | Dubrul et al. |
| 5,766,135 A | 6/1998 | Terwilliger |
| 5,769,795 A | 6/1998 | Terwilliger |
| 5,797,960 A | 8/1998 | Stevens et al. |
| 5,814,064 A | 9/1998 | Daniel et al. |
| 5,935,139 A | 8/1999 | Bates |
| 6,238,412 B1 | 5/2001 | Dubrul et al. |

*Primary Examiner*—Gary Jackson
(74) *Attorney, Agent, or Firm*—James F. Hann; Haynes Beffel & Wolfled LLP

(57) ABSTRACT

A device for the removal of a blockage in a passageway such as a dialysis graft or in a body passageway includes a catheter for reception and aspiration of the blockage and an occlusion engaging element distal of the distal end of the catheter which occlusion engaging element is supported on a wire that extends through the catheter. At the distal end of the catheter, there is a device such as a multi-wing malecot expansion device that is expanded after the catheter is placed in position so as to block the occlusion from passing around the outside of the catheter. The support wire can be a movable core guide wire which has a braided device on its distal end. When the core is as distal as possible of the distal end of the shell, the braid is in a collapsed minimum diameter state for insertion through the catheter and through the occlusion. Proximal movement of the core causes the braid to expand to the wall of the graft. Subsequent proximal movement of the entire support wire causes the braid to contact the occlusion forcing the occlusion into the catheter for aspiration and removal.

16 Claims, 4 Drawing Sheets

TISSUE REMOVAL DEVICE AND METHOD

REFERENCE TO RELATED APPLICATION

This is a continuation of application Ser. No. 09/189,574, filed on Nov. 11, 1998 now U.S. Pat. No. 6,238,412, which application claims the priority of U.S. Provisional Application, Ser. No. 60/065,118, filed on Nov. 12, 1997.

BACKGROUND OF THE INVENTION

In general, this invention relates to a removal device for a biological occlusion and more particularly to a catheter and occlusion engaging element which is adapted to the removal of blockages in hemodialysis grafts.

There are many techniques and devices known in the art for removing blockages in the vascular system and other passageways of the human body.

There is a continuing need for improved devices to meet at least the following objectives.

The first objective is to reduce cost. This is particularly important in recent years where it is clear for safety and sanitary reasons that these will be single use devices. A device, even though it performs a function in some improved manner, will not be widely used if it is considerably more costly than the alternatives available.

A second objective is to provide a device that is simple to use and in a very real sense simple to understand. This will encourage its adoption and use by medical personnel. It will also tend to keep cost low.

The third objective is to provide a device that entails a procedure with which the medical profession is familiar so that the skills that have been learned from previous experience will continue to have applicability.

A fourth objective relates to the effectiveness and thoroughness with which the blockage is removed. It is important that a maximum amount of the blockage be removed; recognizing that no device is likely to provide one-hundred percent removal.

A fifth objective concerns safety; a matter which is often so critical as to trump the other considerations. It is important to avoid tissue trauma. In many circumstances, it is critically important to avoid breaking up a blockage in a fashion that leads to flushing elements of the blockage throughout the body involved.

There are trade-offs in design considerations to achieve the above five interrelated objectives. Extreme simplicity and a very simple procedure might over compromise safety. Addressing all of these considerations calls for some trade-off between the objectives.

Accordingly, a major object of this invention is to provide an improved removal device for a body passageway blockage which achieves the objectives of reduced cost, enhanced simplicity, a standard procedure, high effectiveness and a high degree of safety. Most particularly, it is an object of this invention to achieve these objectives with an enhanced trade-off value for the combined objectives.

BRIEF DESCRIPTION

In brief, one embodiment of this invention is particularly adapted to the removal of blockages in hemodialysis grafts. That embodiment combines a catheter having a blocking feature that blocks the annulus between the catheter and the graft and a support wire having an occlusion engaging element.

The support wire extends through the catheter, through or around the occlusion and at its distal end has an annular braided element attached thereto. The support wire is a dual element support wire having a core and an annular shell that slides on the core. The distal end of the core is attached to the distal end of the annular braided element and the distal end of the shell is attached to the proximal end of the annular braided element. Thus movement of the core and shell relative to one another moves the braided element from a radially retracted position which is useful for insertion through the catheter to a radially expanded position which expands it to the sidewall of the graft. When the annular braided element is in its radially compressed state, it can be passed through the occlusion together with the rest of the wire to reside on the distal end of the occlusion. When the braided element is expanded and moved proximally (that is, in a retrograde fashion), it will engage the occlusion and force the occlusion into the catheter. Alternatively, no motion of the engaging element may be required if aspiration is applied. In this case, the engaging element acts as a seal to prevent the suction from aspiration to remove much material beyond its point of deployment in the channel.

The distal end of the catheter is proximal of the occlusion and contains a blocking mechanism that extends radially from the distal end of the catheter to the wall of the graft or body passageway. This catheter blocking element also has a radially retracted insertion state and a radially expanded blocking state. The blocking element is a multi-wing malecot type device which is covered by a thin elastomeric film or membrane.

This malecot type of device is bonded to the distal end of the catheter or an integral part of the catheter. The distal tip of the dilator, over which the catheter is inserted, has a slightly increased diameter. This tip is in the nature of a ferrule. When the dilator is removed, the ferrule abuts against the distal end of the multi-wing malecot pushing this blocking element from its radially compressed state into its radially expanded state. Alternatively, the tip of the dilator can be bonded to the catheter with a break-away bond so that when the dilator is removed, the blocking element is expanded in a similar fashion. In this radially expanded state, the malecot and its film cover blocks the annulus around the catheter so that the occluded blood or other obstruction which is being removed is forced into the catheter where it is aspirated or otherwise removed.

Conversely, it is understood that the blocking element could be fabricated from tubular braid and the engaging element could be formed from the malecot style configuration.

Figure 2:
FIG. 2 is a longitudinal view of the distal portion of the support wire with a braided occlusion engaging element in its radially compressed state. This is the state where the support wire and engaging element can be inserted through the occlusion that is to be removed.
Figure 3:
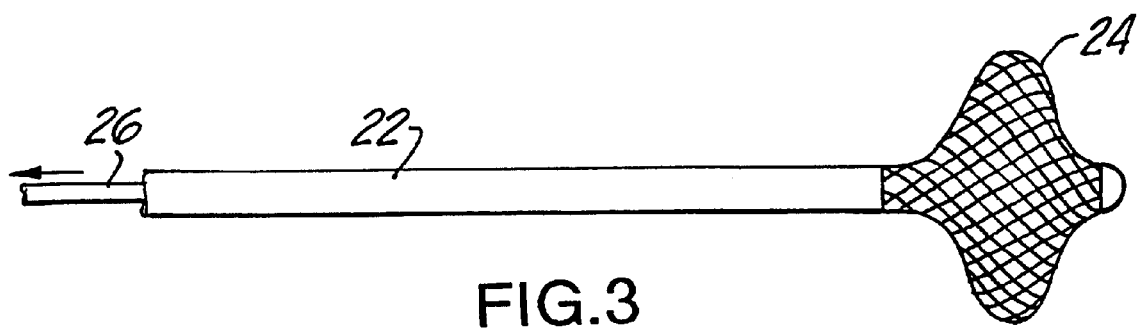
FIG. 3 shows the FIG. 2 braided occlusion engaging element in its radially expanded state, which is the state shown in FIG. 1.
Figure 4:
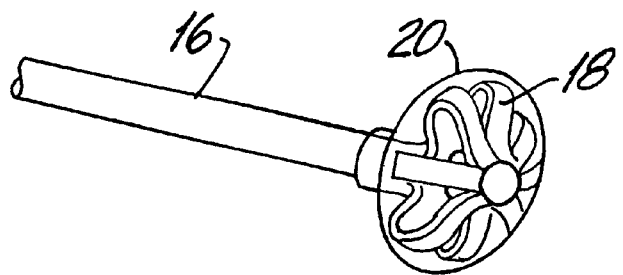
FIG. 4 shows the multi-wing malecot type blocking element at the distal end of the catheter in its radially expanded state, which is the state shown in FIG. 1.

It should be noted that the scale of the FIG. 4 catheter is much reduced compared to the scale of the occlusion removal wire and braided element shown in FIGS. 2 and 3.

Figure 5:
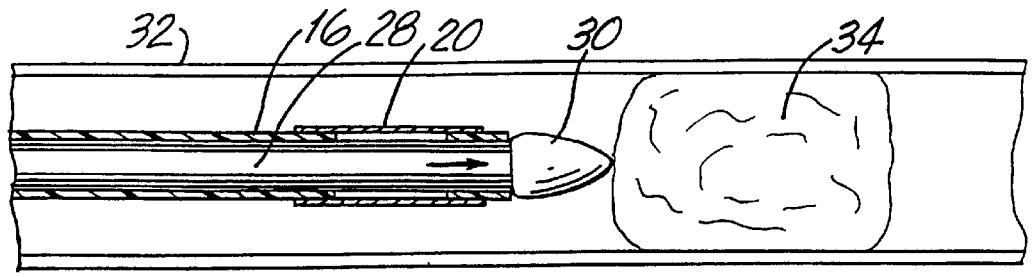

FIG. 5 is a longitudinal view, in partial cross-section, showing the catheter and dilator with a ferrule at the distal tip of the guide wire in a passageway having an occlusion that is to be removed.

Figure 6:
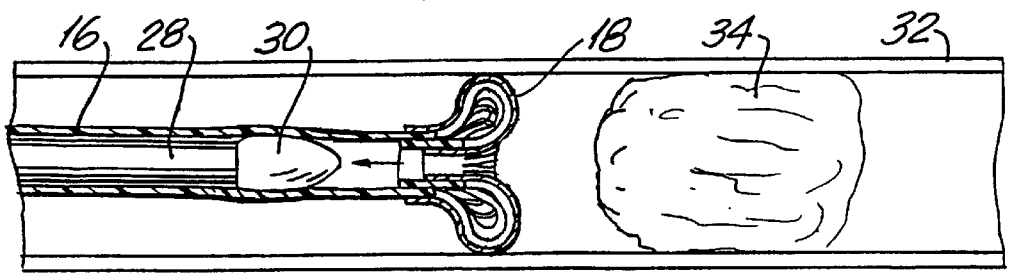

FIG. 6 shows the next step in which the dilator is being removed thereby causing the malecot type blocking mechanism to become expanded by virtue of pressure against the distal end of the catheter tip of the dilator.

Figure 7:
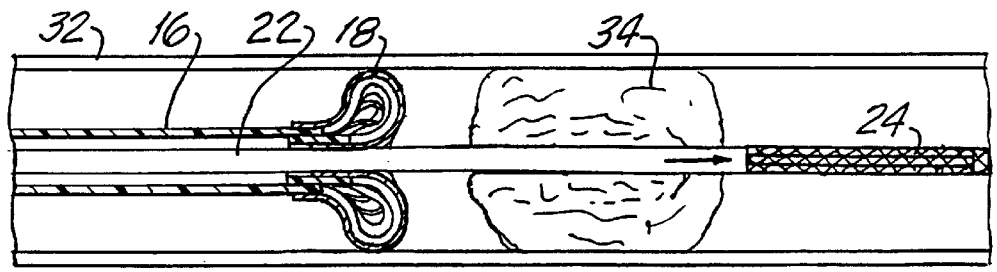

FIG. 7 shows the next step in which the support wire together with the braided occlusion removal element in its radially compressed state (the state shown in FIG. 2) is inserted through the catheter and through the occlusion to be removed.

Figure 8:
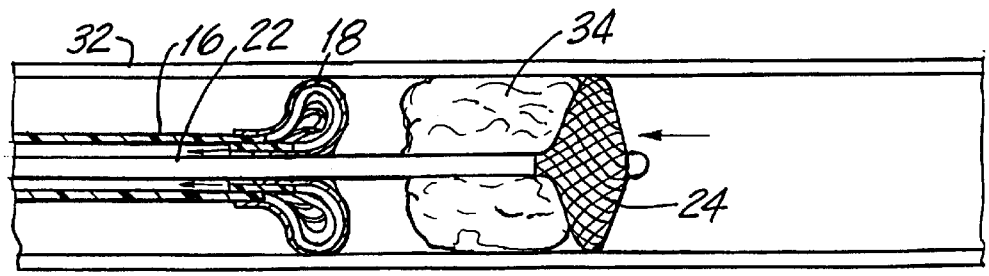

FIG. 8 shows the next step in which the braided occlusion removal element has been expanded and is being pulled in a proximal direction thereby forcing the occlusion into the catheter for removal with or without aspiration.

Figure 9:
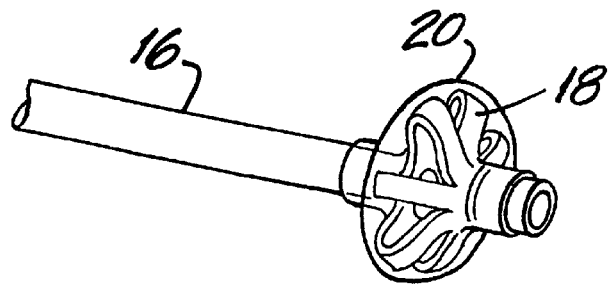

FIG. 9 shows the multi-wing malecot type blocking element at the distal end of the catheter in its radially expanded state in accordance with another embodiment of the present invention.

Figure 10:
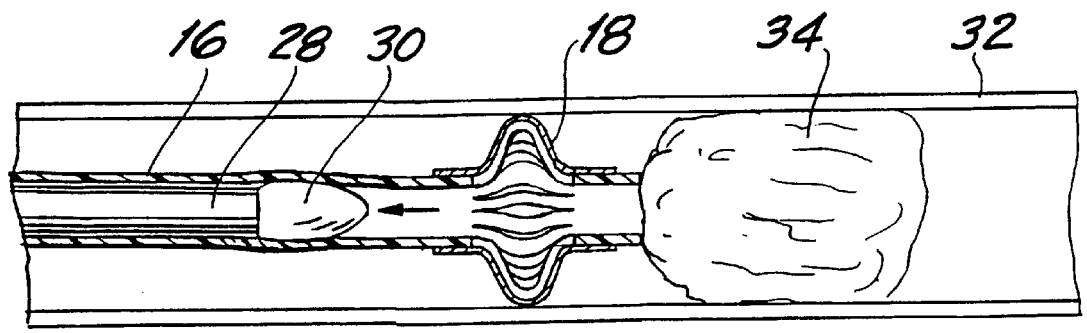

FIG. 10 shows the shape of the expansion resulting from the malecot type blocking element shown in FIG. 9.

DESCRIPTION OF THE PREFERRED EMBODIMENTS

Figure 1:
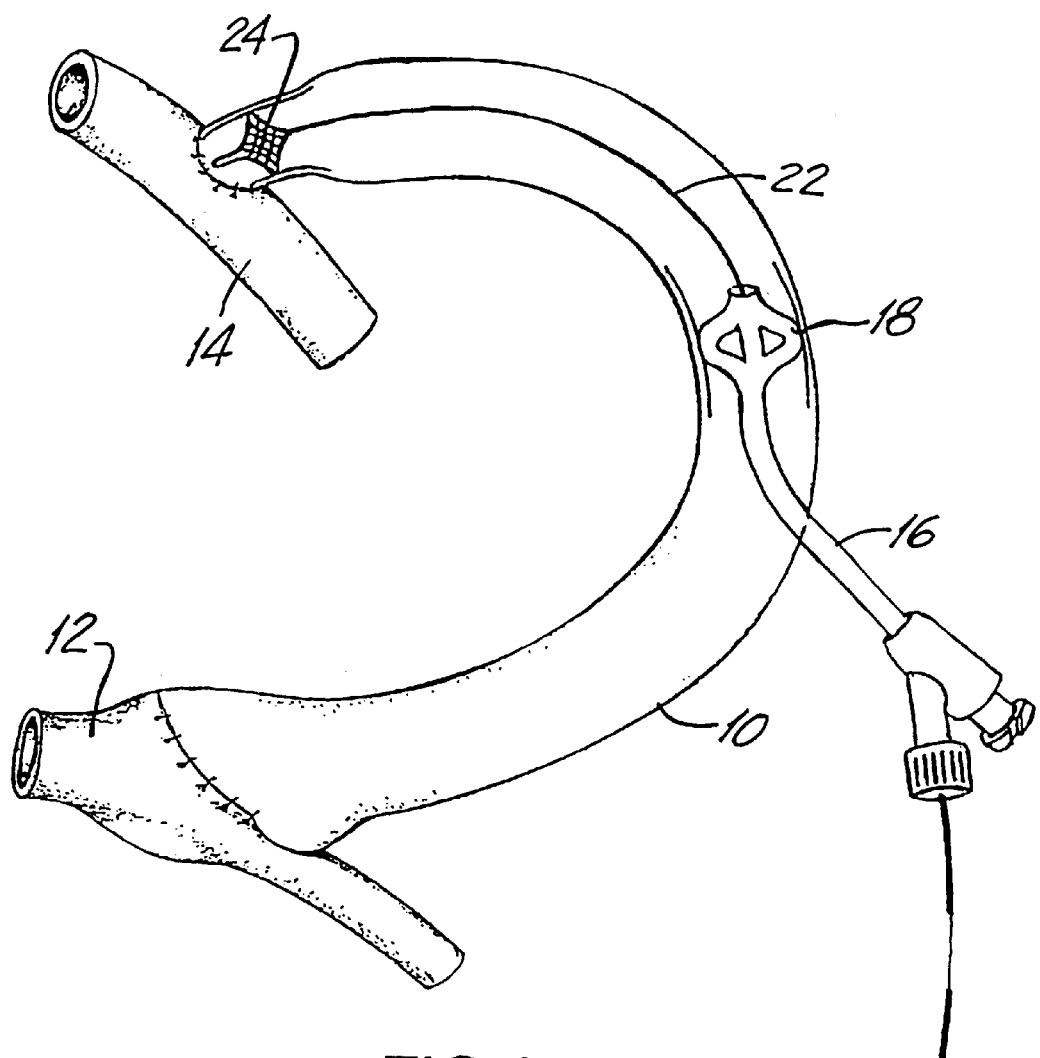
FIG. 1 is a mechanical schematic showing the device of this invention fully deployed in a plastic graft used in hemodialysis. The FIG. 1 drawing shows the blocking element at the distal end of the catheter in its radially expanded state and the occlusion engaging element at the distal end of the support wire in its radially expanded state. It is important to note that the blocking element may take a variety of shapes as would be required for the particular application. The preferred shape is likely to be a funnel shape where the larger diameter is distal to the lesser diameter that is proximal on the element. This funnel shape allows the obstruction to be more easily accepted into the catheter due to the pull/push of the engaging element, aspiration or both.

FIG. 1 shows a typical synthetic graft 10 used in hemodialysis. The graft extends between a vein 12 and an artery 14. The graft 10 may be about thirty centimeters long with an inner diameter (I.D.) of 6 or 7 millimeters. A catheter 16 is inserted through the wall of the graft or vessel. Typically the catheter might have an outside diameter (O.D.) of 2.7 mm and an inner diameter (I.D.) of 2.3 mm. A malecot type expansion device 18 is covered with a membrane 20 (see FIG. 4). When expanded, it serves to block the annular space between the outside wall of the catheter 16 and the graft 10. A support wire 22 for a braided removal mechanism 24 will typically have an outside diameter of about one mm and has an internal actuator rod 26 (see FIG. 2) of approximately 0.5 mm. Because of the simplicity of the design, this outside diameter could be smaller than 0.5 mm. In FIG. 1, the malecot type blocking device 18 and the braided removal device 24 are both shown in their expanded state and are positioned so that retrograde or proximal movement of the support wire 22 will pull the braided element in a proximal direction to push out whatever coagulated blood is between the braided device 18 and the distal end of the catheter into the catheter opening where it can be aspirated; thereby clearing the blockage in the graft or other vessel.

More particularly, one embodiment of this invention which has been partly tested, was designed for use in a hemodialysis graft 10 having an I.D. of approximately six to seven mm. In that case, the catheter 16 has a 8 French O.D. (2.7 mm) and a 7 French I.D. (2.3 mm). The support wire 22 is a fairly standard movable core guide wire of 35 mils (that is, 0.35 inches, which is slightly under 1 mm). The actuator rod 26 in the support wire is approximately 15 mils and thus slightly under 0.5 mm. The braided element 24 has an insertion diameter that is approximately one mm and expands to cover the seven mm diameter of the graft. In order to achieve this seven fold increase in diameter, the braided element has a length of 11 to 13 mm. Thus the catheter has an annulus of about 2.3 mm around the support wire, through which annulus the blood occlusion is aspirated.

FIGS. 2 and 3 illustrate the support wire 22 and braided element 24 which constitute the occlusion engaging element that is moved proximally to push the occlusion into the catheter for removal. A preferred occlusion engaging element 24 is a braided element. The braided material has to have a stiffness such that it will not collapse or fold under the pressure of the occlusion when this engaging element is being moved proximally. Yet the filaments that form the braid must be flexible enough to be moved between the two states as shown in FIGS. 2 and 3. Materials from polyester to stainless steel can be successfully used. A more detailed teaching of the considerations that go into the selection of the braided engaging element is set forth further on.

The distal tip of the braided element 24 is connected to the distal tip of the actuator rod 26. The proximal edge of the braided element 24 is bonded to the distal end of the support wire 22. Thus when the actuator rod 26 is pushed in a distal direction relative to the wire 22, the braided device is forced into its collapsed state shown in FIG. 2 and is available to be pushed through the catheter and through or around the occlusion which is to be removed. When this engaging element 24 has been fully inserted, the actuator rod 26 is moved in a proximal direction causing the braided element 24 to take the expanded position such as that shown in FIG. 3 so that subsequent movement of the entire support wire 22 will cause the braided element to move against the occlusion and push the occlusion into the distal end of the catheter. In some circumstances, the braided element 24 might be left as a braid with openings because the portions of the occlusion which may pass through the openings will be sufficiently smaller liquids so that they do not have to be removed. In other circumstances, it might be desirable to cover the braided element 24 with a membrane or film so that it becomes substantially impermeable. Further the membrane or film covering the engaging element will be helpful in preventing trauma to the inner walls of native tissue. Even further, this membrane may be helpful in optimizing the physical characteristics of the engaging element.

With reference to FIG. 1, it might be noted that when the braided element is pushed all the way down to one end of the graft 10, as shown in FIG. 1, and then expanded it will be expanding against a portion of the wall of the graft that is smaller than the bulk of the graft. However, as the support wire 22 is pulled to move the braided occlusion removal element proximally, the braided occlusion element rides on the wall of the graft and will expand as the wall of the graft expands as long as tension is maintained on the actuator rod 26.

There might be applications of the invention where the passageway involved is a tissue passageway such as a blood vessel or other channel within the body, where this braided element 24 is expanded to nearly the diameter of the vessel so that when it is moved to push out an occlusion, it will avoid trauma to the wall of the vessel. Further, the membrane on the expanding element will aid in decreasing the trauma to native vessels as described above. In such a case, the engaging element (and the blocking element) may be used only as a 'seal' so that the obstruction may be removed or otherwise obliterated. This seal allows the rest of the vessel to be uncontaminated and provides for a 'closed system' for irrigation and/or aspiration and subsequent obliteration or removal of the obstruction.

FIG. 4 illustrates the catheter 16 with the malecot 18 in an expanded state on the distal end of the catheter. A membrane 20 is normally used in order to provide a complete blocking or sealing function. Further, the membrane 20 may aid in locking the blocking element in a particular shape. This malecot type element is created by making longitudinal slits in the sidewall of the catheter (or an attachment bonded thereto) thereby creating links or wings that will expand when the distal end of the catheter is pushed in a proximal direction. The appropriate pushing of the proximal end of the catheter is achieved, as shown in FIG. 5, by a ferrule 30 which is a standard tip on a standard dilator 28. Alternatively, the dilator 28 may be a guide wire (which is usually much longer and flexible than a dilator) for remote obstruction removal. In such an application of the present invention, the guide wire would have a ferrule type mechanism that would act like the ferrule on the dilator. In this instance, the guide wire (with ferrule) would be inserted into the vessel to the obstruction. The catheter would then be pushed along the guide wire until it reached the ferrule which would normally be located near the distal end of the guide wire. At this point the wire would be pulled back, the ferrule would butt against the catheter and force out the blocking/sealing element. The engaging element may be used with this blocking element and it could even be the ferruled wire as well.

It should be noted that the retention catheter described in U.S. Pat. No. 3,799,172 issued on Mar. 26, 1974 to Roman Szpur illustrates a structure that is similar to the malecot type device 18 illustrated in FIG. 4; although in that patent it is used as a retention device whereas in this invention it is used as a blocking element.

This blocking element 18 is often called a malecot in the industry. It should be understood herein that the term malecot is used to refer in general to this type of multi-wing device.

More specifically, as shown in FIG. 5, the catheter 16 together with a dilator 28 having an expanded tip 30 which is a ferrule is inserted into a vessel 32 such as the graft shown in FIG. 1. The catheter 16 and dilator 28 are inserted close to the occlusion 34 and then the dilator 28 is removed. Proximal motion of the dilator 28 causes the tip 30 to contact the distal end of the catheter 16 forcing the distal end of the catheter to put pressure on the malecot wings creating the expansion shown in FIG. 6 (and also schematically shown in FIG. 1). Once this expansion has occurred, the dilator with its tip can be removed from the catheter (as shown in FIG. 6).

What then occurs is shown in FIGS. 7 and 8. As shown in FIG. 7, the support wire 22 with its braided removal element 24 is inserted in the collapsed state so that it passes through or around the occlusion 34. It should be noted that the support wire 24 may be inserted prior to the blocking catheter being inserted or after the catheter is inserted (the latter of which is illustrated in the figures). Most of the occlusions to which this invention is directed such as congealed blood in a graft will permit a support wire 22 to pass through it because the consistency is that of viscous material which can be readily penetrated. Alternatively, if the occlusion is a non viscous material such as a stone, plaque, emboli, foreign body, etc. the support wire 22 is small enough to be passed around the occlusion. Once the braided element 24 is on the distal side of the occlusion 34, the actuator rod 26 is pulled creating the expanded state for the braided device. Accordingly, distal movement of the entire support wire will cause the expanded braided device to move against the occlusion and force it into the catheter for removal with or without aspiration. When removal of obstructions that are located some distance away from the point of access into the body such as the carotid artery via a groin access the wire 22 would likely be inserted first. In this case the support wire 22 with its expanding element 24 may be used as a guide wire to guide the catheter to the preferred location. Of further import is that the blocking element and the engaging element may be used without any relative motion once deployed. Such is the case when irrigation and/or aspiration is used for the obstruction removal. In this case the two elements can be used as seals against the tubular inner walls on both sides of the obstruction whereby the obstruction is removed from that 'sealed' space with the use of aspiration, irrigation, or both. Further other means of obliterating the obstruction within this 'sealed' space may be employed. Some of those means are, but are not limited to the addition of dissolving agents, delivery of energy such as ultrasound, laser or light energy, hydraulic energy and the like.

The Tubular Braid Engaging Element

The engaging apparatus includes an elongate tube; an elongate mandril inside the tube and an expandable tubular braid. The elongate mandril extends from the proximal end of the device to the distal end. The elongate tube extends from close to the proximal end of the device to close to the distal end. The distal end of the tubular braid is bonded to the distal end of the inner elongate mandril. The mandril may extend beyond the tubular braid. The proximal end of the tubular braid is bonded to the distal end of the elongate tube.

The braid may be open, but may be laminated or covered with a coating of elastic, generally inelastic, plastic or plastically deformable material, such as silicone rubber, latex, polyethylene, thermoplastic elastomers (such as C-Flex, commercially available from Consolidated Polymer Technology), polyurethane and the like. The assembly of tube, mandril and braid is introduced percutaneously in its radially compressed state. In this state, the outside diameter of the braid is close to the outside diameter of the elongate tube. This diameter is in the range of 10 to 50 mils, and usually 25 to 40 mils (i.e. thousandth of an inch). After insertion, the tubular braid is expanded by moving the mandril proximally with respect to the tube.

The tubular braid is preferably formed as a mesh of individual non-elastic filaments (called "yarns" in the braiding industry). But it can have some elastic filaments interwoven to create certain characteristics. The non-elastic yarns can be materials such as polyester, PET, polypropylene, polyamide fiber (Kevlar, DuPont), composite filament wound polymer, extruded polymer tubing (such as Nylon H or Ultem, commercially available from General Electric), stainless steel, Nickel Titanium (Nitinol), or the like so that axial shortening causes radial expansion of the braid. These materials have sufficient strength so that the engaging element will retain its expanded condition in the lumen of the body while removing the obstruction therefrom.

The braid may be of conventional construction, comprising round filaments, flat or ribbon filaments, square filaments, or the like. Non-round filaments may be advantageous to decrease the axial force required for expansion to create a preferred surface area configuration or to decrease the wall thickness of the tubular braid. The filament width or diameter will typically be from about 0.5 to 25 mils, usually being from about 5 to 10 mils. Suitable braids are commercially available from a variety of commercial suppliers.

The tubular braids are typically formed by a "Maypole" dance of yarn carriers. The braid consists of two systems of yarns alternately passing over and under each other causing a zigzag pattern on the surface. One system of yarns moves helically clockwise with respect to the fabric axis while the other moves helically counter-clockwise. The resulting fabric is a tubular braid. Common applications of tubular braids are lacings, electrical cable covers (i.e. insulation and shielding), "Chinese hand-cuffs" and reinforcements for composites. To form a balanced, torque-free fabric (tubular braid), the structure must contain the same number of yarns in each helical direction. The tubular braid may also be pressed flat so as to form a double thickness fabric strip. The braid weave used in the tubular braid of the present invention will preferably be of the construction known as "two dimensional, tubular, diamond braid" that has a 1/1 intersection pattern of the yarns which is referred to as the "intersection repeat". Alternatively, a Regular braid with a 2/2 intersection repeat and a Hercules braid with an intersection repeat of 3/3 may be used. In all instances, the helix angle (that being the angle between the axis of the tubular braid and the yarn) will increase as the braid is expanded. Even further, Longitudinal Lay-Ins can be added within the braid yarns and parallel to the axis to aid with stability, improve tensile and compressive properties and modulus of the fabric. When these longitudinal "Lay-In" yarns are elastic in nature, the tubular braid is known as an elastic braid. When the longitudinal yarns are stiff the fabric is called a rigid braid. Biaxially braided fabrics such as those of the present invention are not dimensionally stable. This is why the braid can be placed into an expanded state from a relaxed state (in the case of putting it into the compressive mode). Alternatively this could be a decreased/reduced (braid diameter decreases) state when put into tension from the relaxed state. When put into tension (or compression for that matter) the braid eventually reaches a state wherein the diameter will decrease no more. This is called the "Jammed State". On a stress strain curve, this corresponds to increase modulus. Much of the engineering analysis concerning braids are calculated using the "Jammed state" of the structure/braid. These calculations help one skilled in the art to design a braid with particular desired characteristics. Further, material characteristics are tensile strength, stiffness and Young's modulus. In most instances, varying the material characteristics will vary the force with which the expanded condition of the tubular can exert radially. Even further, the friction between the individual yarns has an effect on the force required to compress and un-compress the tubular braid. For the present invention, friction should be relatively low for a chosen yarn so that the user will have little trouble deploying the engaging element. This is particularly important when the engaging element is located a significant distance from the user. Such is the case when the percutaneous entry is the groin (Femoral Artery for vascular interventions) and the point of engaging the engaging element is some distance away (i.e. the Carotid Artery in the neck). Similarly, this is true for long distances that are not vascular or percutaneous applications.

Other Comments

An important consideration of the invention described herein is that the support wire with its expanding element can be fabricated with a very small diameter. This is important because it allows an optimally large annular space between the wire and the inside of the catheter for maximum obstruction removal. Previous engaging elements have been used that use a balloon for the engaging element. This balloon design requires a larger shaft diameter than that of the present invention. Hence in these previous devices the annular space is not maximized as in the present invention. The term wire is used to refer to the support portion of the removal device. The material of the wire need not necessarily be metal. Further, it may be desirable to use a 'double' engaging element (i.e. two braided or malecot expanding elements separated a distance appropriate to entrap the occlusion) in the case for example where the occlusion is desired to be trapped in the vessel. The term wire is used herein to refer to a dual element device having a shell component and a core or mandril component which are longitudinally moveable relative to one another so as to be able to place the braided occlusion engaging element into its small diameter insertion state and its large diameter occlusion removal state.

Although the blocking element is described as a multi-malecot type of device, it should be understood that the blocking element may be designed in various fashions which are known in the art. See, for example, FIGS. 9 and 10. As another example, an appropriately designed braid arrangement could be used as the blocking element. In that case, the catheter may have to be a dual wall catheter in which the inner and outer annular walls are able to move relative to one another in a longitudinal direction so as to place the braid used as a blocking element in its small diameter insertion state and its large diameter blocking state. Alternatively, it may be a single wall similar in design to the malecot style blocking element described previously.

The particular embodiment disclosed was designed for an application to remove congealed blood in a dialysis graft. For some applications, like removing clots from remote vascular areas, the blocking mechanism and engaging elements may be used only as distal and proximal seals around the device to be removed so that the clot or other obstruction can be removed with aspiration or can be obliterated with some therapy such as a chemical dissolving agent or acoustical energy or lithotripsy and the like. The residual obstruction in that case would be aspirated from the tubular catheter.

It should be further understood that there might be a situation in which the is blocking element or even the occlusion engaging element would be provided to the physician in a normal expanded state so that when the device is deployed, it would, through plastic memory or elastic memory, automatically snap into its expanded state.

What is claimed is:

1. A medical instrument for use in a body comprising:
   an elongate tubular member having a lumen and a distal end,
   a multi-wing blood flow blocking element positioned near said distal end of said elongate member,
   an annular membrane around said wings of said multi-wing blood flow blocking element,
   said multi-wing blood flow blocking element having a radially compressed state and a radially expanded blocking state,
   an actuator associated with said elongate member to move said blood flow blocking element from said compressed state and to said blocking state,
   said multi-wing blood flow blocking element in said radially expanded blocking state having a generally funnel shape surface extending from said distal end of said elongate tubular member.

2. The medical instrument of claim 1 wherein said multi-wing blood flow blocking element is a malecot style device.

3. The medical instrument of claim 1 wherein said membrane is an elastomeric, impermeable membrane.

4. The medical instrument of claim 2 wherein said membrane is an elastomeric, impermeable membrane.

5. The medical instrument of claim 1 wherein said actuator extends, through said lumen, distal of said blood flow blocking element and when moved in a proximal direction, engages said blood flow blocking element to switch said blood flow blocking element from said retracted compressed state into said radially expanded state.

6. An occluder for use in a body passageway comprising:
a catheter having a distal end,
a multi-wing blood flow blocking element positioned near the distal end of the catheter, and
an annular membrane around said wings of said blood flow blocking element,
said multi-wing blood flow blocking element having a radially compressed insertion state and a radially expanded blocking state,
an actuator associated with said catheter to move said blood flow blocking element from said compressed state to said expanded state.

7. The occluder of claim 6 wherein said multi-wing blood flow blocking element is a malecot style device.

8. The occluder of claim 6 wherein said membrane is an elastomeric, impermeable membrane.

9. The occluder of claim 7 wherein said membrane is an elastomeric, impermeable membrane.

10. The occluder of claim 6 wherein said blood flow blocking element in said radially expanded blocking state has a generally funnel surface extending out from said distal end of said catheter.

11. The occluder of claim 10 wherein said multi-wing blood flow blocking element is a malecot style device.

12. The occluder of claim 11 wherein said membrane is an elastomeric, impermeable membrane.

13. The occluder of claim 6 wherein said actuator extends, through said lumen, distal of said blood flow blocking element and when moved in a proximal direction, engages said blood flow blocking element to switch said blood flow blocking element from said retracted insertion state into said radially expanded blocking state.

14. The occluder of claim 13 wherein said dilator extends, through said lumen, distal of said blood flow blocking element and when moved in a proximal direction, engages said blood flow blocking element to switch said blood flow blocking element from said retracted insertion state into said radially expanded blocking state.

15. The method of deploying an occluder in a body passageway comprising the steps of:
inserting a catheter into a body passageway, said catheter having a malecot-style blood flow blocking device covered with an annular elastomeric, impermeable membrane,
providing said blood flow blocking element in a radially compressed state during said step of inserting, and
radially expanding said blood flow blocking element into a radially expanded state extending to or near to the wall of the body passageway after said step of inserting, and
using said expanded state of said blood flow blocking element for blocking passage of material around the outside of said catheter.

16. The method of claim 15 wherein said steps of radially expanding includes providing said expanded state with a generally funnel surface extending out from said distal end of said catheter.

* * * * *